United States Patent [19]
Centa et al.

[11] Patent Number: 5,390,670
[45] Date of Patent: Feb. 21, 1995

[54] FLEXIBLE PRINTED CIRCUIT SENSOR ASSEMBLY FOR DETECTING OPTICAL PULSES

[75] Inventors: John A. Centa, Euclid; Laszlo Halasz, Brecksville, both of Ohio

[73] Assignee: Gould Electronics Inc., Eastlake, Ohio

[21] Appl. No.: 139,564

[22] Filed: Oct. 20, 1993

Related U.S. Application Data

[62] Division of Ser. No. 870,247, Apr. 17, 1992, Pat. No. 5,263,244.

[51] Int. Cl.⁶ .............................................. A61B 5/00
[52] U.S. Cl. ................................... 128/633; 128/664; 128/665; 128/666; 356/41
[58] Field of Search ................ 128/633, 632, 664–666; 356/39–41

[56] References Cited

U.S. PATENT DOCUMENTS

| | | |
|---|---|---|
| 4,715,928 | 12/1987 | Hamby . |
| 4,819,752 | 4/1989 | Zelin . |
| 4,865,038 | 9/1989 | Rich et al. . |
| 4,938,218 | 7/1990 | Goodman et al. . |
| 4,960,126 | 10/1990 | Conlon et al. . |
| 4,964,408 | 10/1990 | Hink et al. . |
| 4,974,591 | 12/1990 | Awazu et al. ................ 128/633 |
| 5,001,604 | 3/1991 | Lusby . |
| 5,041,187 | 8/1991 | Hink et al. . |
| 5,069,213 | 12/1991 | Polczynski ................... 128/633 |
| 5,094,240 | 3/1992 | Muz ............................ 128/633 |
| 5,097,101 | 3/1992 | Trobough . |

FOREIGN PATENT DOCUMENTS

| | | |
|---|---|---|
| 0357249 | 3/1990 | European Pat. Off. . |
| 0481612A1 | 4/1992 | European Pat. Off. . |
| 3809084A1 | 9/1989 | Germany . |

Primary Examiner—Angela D. Sykes
Attorney, Agent, or Firm—Michael A. Centanni

[57] ABSTRACT

A flexible sensor assembly for detecting optical pulses in which said sensor assembly comprises a flexible printed circuit having mounted thereon at least one light emitting diode and at least one photoelectric detector connected to different circuit patterns with an insulative tape secured over the circuit and components and wherein the flexible sensor is adapted to be folded so that the photoelectric detector can be spaced from and disposed over the light emitting diode.

10 Claims, 4 Drawing Sheets

FLEXIBLE PRINTED CIRCUIT SENSOR ASSEMBLY FOR DETECTING OPTICAL PULSES

This application is a division of prior U.S. application Ser. No. 07/870,247, filed on date Apr. 17, 1992, now U.S. Pat. No. 5,263,244.

FIELD OF THE INVENTION

The invention relates to a flexible sensor assembly for detecting optical pulses in which said sensor assembly comprises a flexible printed circuit having mounted thereon at least one light emitting diode and at least one photoelectric detector connected to different circuit patterns with an insulative tape secured over the circuit and components and wherein the flexible sensor assembly is adapted to be folded so that the photoelectric detector can be spaced from and disposed over the light emitting diode.

BACKGROUND OF THE INVENTION

A pulse oximeter measures the oxygen level of blood by transmitting two different wavelengths of light through a portion of a subject's body where arterial blood is flowing. Conveniently this may be a finger or earlobe. The light which is transmitted through a patient's body is detected by a photodetector which produces a current that is a function of the pulsatile blood flow. The current produced is in response to each wavelength of light that is measured from the patient's body and these measurements may be combined by well-known algorithms such a Bier-Lambert's to produce a quantification of the oxygen content of the blood.

U.S. Pat. No. 2,706,927 discloses the computation of oxygen saturation from measurements of light absorption of body tissue at two wavelengths. A series of devices and procedures have been found using this technology. Generally a required peripheral device of a pulse oximeter is a photoelectric probe. Typically, such a probe is clamped to an appendage of a patient's body, such as an ear or a finger as stated above. Such probes require at least one light source for directing light into the appendage and at least one sensor for receiving light diffused out of the appendage. One method of obtaining light of the desired frequency has been to use a light source of indeterminate wavelength range in combination with a monochromatic filter of known bandpass.

U.S. Pat. No. 4,819,752 discloses a device having means for sensing electromagnetic energy of at least two wavelengths as it passes through a portion of a patient's body and means for processing the signals so produced so as to separate out a pulsatile portion of each signal which is related to the physiological pulse, and then determine the percent saturation as a function of the relative sizes of the pulsatile and non-pulsatile components.

Non-invasive photoelectric pulse oximetry have been used for a number of years and are supplied by several manufacturers. Typically, pulse oximeters measure and display various blood flow characteristics including but not limited to blood oxygen saturation of hemoglobin in arterial blood, volume of individual blood pulsations supplying the flesh, and the rate of blood pulsation corresponding to each heartbeat of the patient. The oximeter passes light through human or animal body tissue where blood perfuses the tissue such as a finger, an ear, the nasal septum or the scalp, and photoelectrically senses the absorption of light in the tissue. The amount of light absorbed is then used to calculate the amount of blood constituent being measured. The light passed through the tissue is selected to be of one or more wavelengths that is absorbed by the blood in an amount representative of the amount constituent present in the blood.

As stated above, generally pulse oximeters require a peripheral device such as a photoelectric probe that can be clamped to an appendage of a patient's body. The photoelectric probe generally comprises a flexible circuit board mounted with a photodetector at one end and at least one light emitting diode spaced apart from the photodetector so that the circuit board can be folded to align the photodetector over the light emitting diode. One photoelectric probe comprises a printed circuit on a flexible substrate composed of a first circuit having a photodetector mounted across terminals of the first circuit and wherein an opening is provided between the terminals so that the photodetector is exposed on the side of the substrate that does not contain the printed circuit. In a like manner a second circuit is disposed on the substrate in which two parallel connected light emitting diodes are mounted across terminals of the second circuit and wherein an opening is provided between the terminals so that the diodes are exposed on the side of the substrate that does not contain the printed circuit. The probe is then folded so that the side of the substrate that does not contain the printed circuit is facing inwardly and the photodetector disposed through the opening faces the diodes exposed through the second opening. This arrangement of the probe places stress on the solder connection of the components to the printed circuit and requires exact precision for mounting of the components over the openings in the substrate.

It is an object of the present invention to provide a flexible sensor assembly for detecting optical pulses that does not require forming an opening in the substrate for the sensor components and which has a non-conductive film secured over the components and circuitry of the sensor to prevent shorting of the circuitry during use.

It is another object of the present invention to provide a flexible sensor assembly for detecting optical pulses that is easy to produce and cost effective to manufacture.

It is another object of the present invention to provide a method for producing flexible sensor assemblies for detecting optical pulses.

SUMMARY OF THE INVENTION

The invention relates to a flexible sensor assembly for detecting optical pulses comprising a flexible sheet containing conductive circuitry secured thereon, said conducted circuitry comprising a first pair of conductive strips insulated from each other and extending at one end to provide a first set of terminals and at the other end to provide a second set of terminals, and a second pair of conductive strips insulated from each other and from the first pair of conductive strips and extended at one end to provide a first set of terminals and at the other end to provide a second set of terminals with said second set of terminals spaced apart from the second set of terminals of the first pair of conductive strips; at least one photodetector mounted across said first set of terminals of the first pair of conductive strips, at least one light emitting diode mounted across said first set of terminals of the second pair of conductive strips; an insulative tape secured over the photodetector, light emitting diode and the circuitry at least up to the second set of terminals of said first and second pair of conductive strips; and wherein said flexible sensor is capable of being folded so that the photodetector can be spaced from and disposed over the light emitting diode.

In the preferred embodiment, two light emitting diodes would be connected in parallel across the first set of terminals of the second pair of conductive strips. One diode would be a red light emitting diode and the other diode would be an infra-red light emitting diode. The light emitting diode would preferably emit light at wavelengths of 600 nanometers for the red light emitting diode and 940 nanometers for the infra-red light emitting diode. The photodetector could be a planar photodiode, such as a silicon photodiode, that would measure the intensity of the red and infra-red light passing through pulsating vascular tissue.

The invention also relates to a method for producing flexible sensor assemblies for use in detecting optical pulses comprising the steps:
  (a) forming onto a copper coated flexible sheet a layer of a design comprising a plurality of circuits in which each circuit comprises a first pair of spaced apart strips extending at one end to provide a first set of terminals and at the other end to provide a second set of terminals, and a second pair of spaced apart strips extending at one end to provide a first set of terminals and at the other end to provide a second bet of terminals;
  (b) etching and removing the exposed copper on the copper coated flexible substrate that is not covered by said layer and then removing said layer leaving a plurality of copper circuits;
  (c) securing at least one photodetector component across the first set of terminals of the first pair of spaced apart copper strips of each circuit and securing at least one light emitting diode component across the first set of terminals of the second pair of spaced apart copper strips of each circuit;
  (d) securing a layer of non-conductive film across the plurality of circuits and components at least up to the second set of terminals of each circuit; and
  (e) cutting each circuit with its mounted components from the sheet to produce a single flexible sensor that can be folded so that the photodetector component can be spaced from and disposed over the light emitting diode component.

The preferred flexible sheet or substrate for the sensor would be a plastic sheet such as a polyamide or polyester sheet, with a thickness of from 0.0015 inch to 0.010 inch, preferably from 0.003 inch to 0.005 inch and most preferably from 0.0048 inch to 0.0052 inch. The preferred plastic sheet would be a Mylar sheet which is a trademark of E.I. duPont de Nemours and Company for polyethylene terephthalate resin or a Kapton sheet which is a tradename for polyamide synthetic fiber. The flexible sheet is then laminated or coated with copper to a desired thickness such as from 0.0003 to 0.003 inch thick copper. For the purpose of this invention, a copper laminated onto a polyester sheet shall be referred to as a polyester sheet coated with a copper layer. A photoresist such as photopolymer film sold under the trademark Riston 4200 series of E.I. duPont de Nemours and Company or the trademark Laminar HG 15 of Morton Thiokol, Inc.-Dynachem Division is then deposited on the copper and using an appropriate artwork for a plurality of circuits along with an ultra-violet light source, a plurality of circuits can be developed on the photoresist coated copper. The flexible printed circuit sheet can then be etched with a solution such as cupric chloride to remove copper not covered by the developed photoresist. Upon removal of the photoresist by stripping, a flexible printed circuit sheet is produced that is ready to receive surface mounted components. Conductive epoxy can then be dispensed on the terminals of the circuitry where the components will be mounted. The components could be mounted on the flexible printed circuit sheet using automation machinery. The conductive epoxy could be cured using heat or ultra-violet light. After assembly of the components on the appropriate terminals of the circuitry, a non-conductive sheet is secured over the components and the circuitry to protect the circuitry from shorting or other damage. The preferred non-conductive sheet should be transparent to the wavelength of the longest emitting diode and could be polytetrafluoroethylene tape preferably having a thickness from 0.0005 inch to 0.003 inch. The individual circuits could then be cut or punched out using a conventional driven punch and die.

When the flexible sensor is to be used on a finger of a patient then a suitable pouch is provided which has an opening sufficient to accommodate a finger and the flexible sensor could be folded and mounted within the pouch. Preferably, the interior of the pouch would have a channel into which the flexible sensor could be seated.

Although the components of the sensor could be secured to the printed circuit sheet using solder, the use of conductive epoxy is preferred since conductive epoxy cures at a lower temperature than solder, thereby effectively eliminating thermal shock to the components which could occur by the higher temperatures associated with soldering. By eliminating the need for cut outs in the printed circuit sheets, the components can be secured flush to the printed circuit sheet thereby providing them with more physical support to the sheet. The use of the non-conductive sheet overlay on the circuit and components provides for electrical isolation, effectively minimizes the moisture problem of previous sensor designs and additional protection to the components. The non-conductive sheet overlay has to be transparent to the light emitted from the diodes. The overall design of the flexible sensor enables robotic component placement machines to assemble the components onto the printed circuit sheet thereby providing a cost effective method for producing the sheet.

The foregoing and other steps, features and advantages of the invention will be apparent from the following more particular description of preferred embodiments of the invention as illustrated in the accompanying drawings.

DETAILED DESCRIPTION OF THE INVENTION

Figure 1:
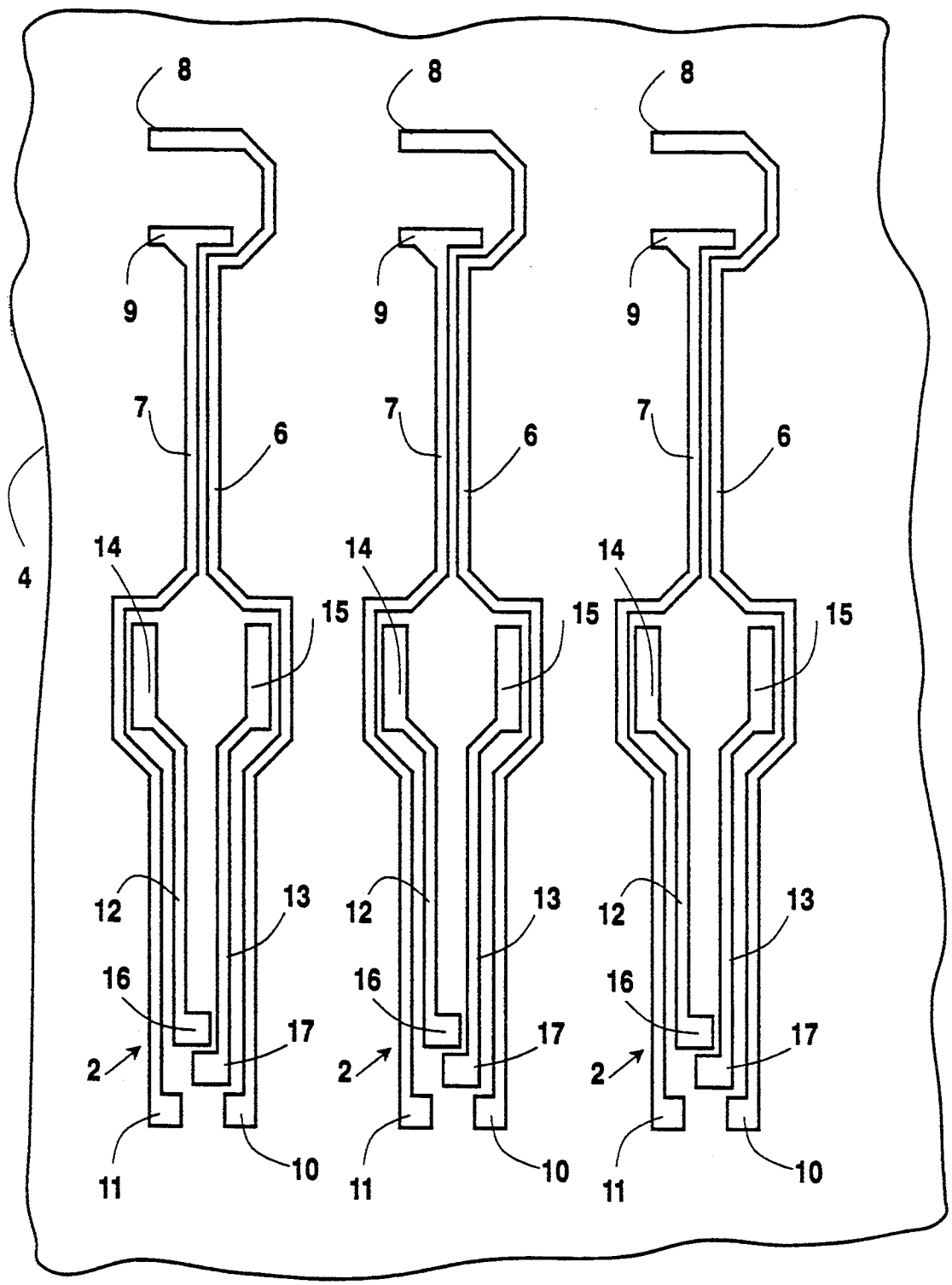
FIG. 1 is a plan view of a printed circuit sheet showing an example of a plurality of printed circuits.

FIG. 1 shows a plurality of individual circuits 2 secured to a polyester sheet 4. The plurality of circuits 2 are formed on the polyester sheet using conventional printed board technology. Specifically by way of example, a copper sheet is laminated or deposited onto the polyester sheet 4 and then a photoresist is deposited or laminated over the copper. An appropriate artwork is used to project onto the photoresist a plurality of circuit images. The image is developed in a conventional manner and then the excess copper is removed by etching using a solution such as cupric chloride. With the excess copper removed, only the design of the plurality of circuits remain and when the photoresist is stripped off, a printed circuit sheet is produced having a plurality of copper circuits 2. Each circuit 2 contains a first pair of spaced apart copper strips 6 and 7 terminating at one end with terminals 8 and 9 and at the other end with terminals 10 and 11. Each circuit 2 also contains a second pair of spaced apart copper strips 12 and 13 terminating at one end with terminals 14 and 15 and at the other end with terminals 16 and 17.

As shown in FIG. 1, terminals 8 and 9 are designed to accommodate the surface mounting of a component such as the photodetector component while terminals 14 and 15 are designed to accommodate the surface mounting of a component such as light emitting diodes. If desired, the light emitting diodes could be mounted across terminals 8 and 9 and the photodetector could be mounted across terminals 14 and 15. Terminals 10-11 and terminals 16-17 are used to make electrical connection to an oximeter.

Figure 2:
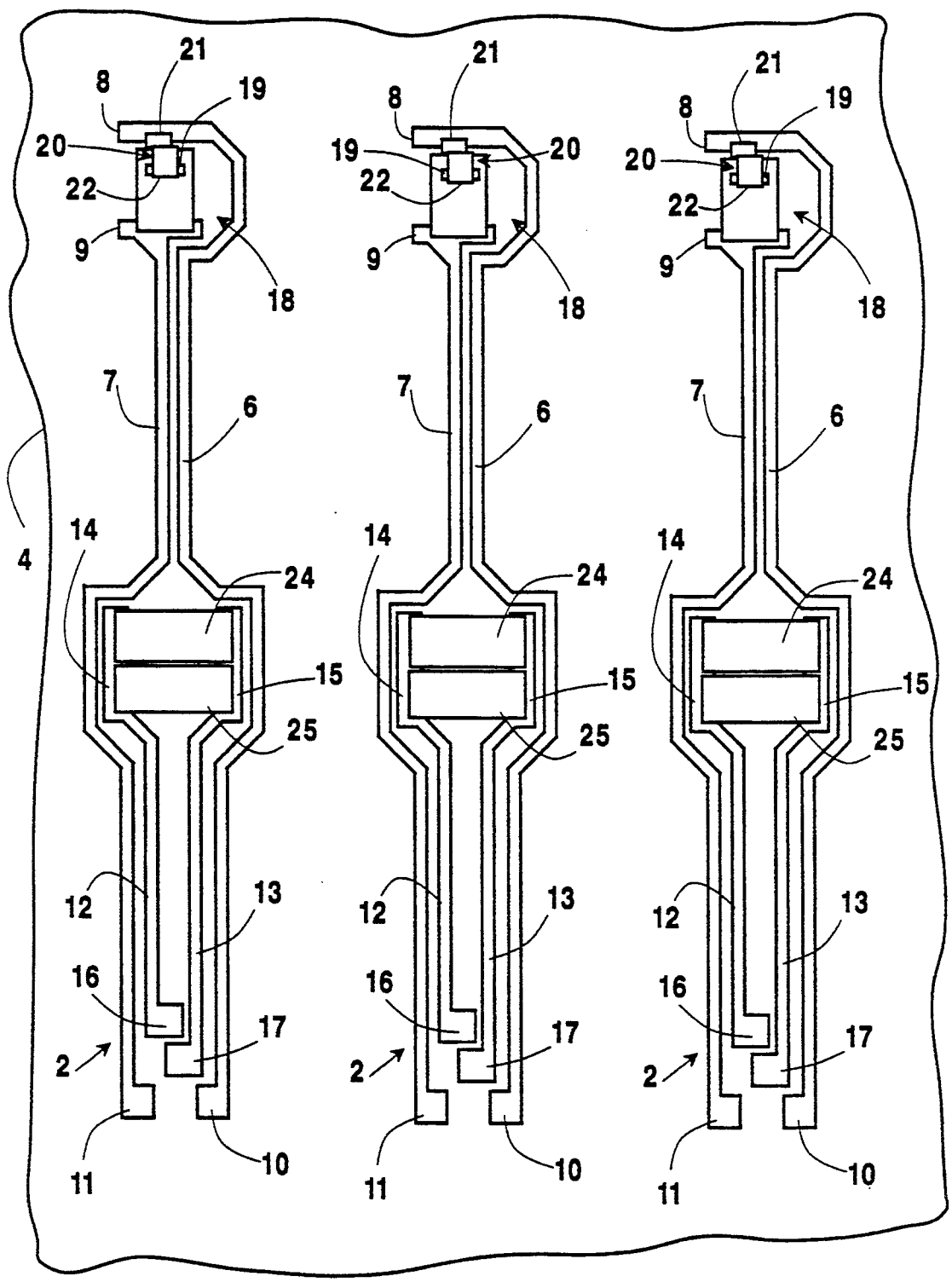
FIG. 2 is a plan view of the printed circuit sheet of FIG. 1 showing surface mounted components secured across the terminals of the circuits.

FIG. 2 shows the printed circuit sheet of FIG. 1 with identical components identified with the same reference numbers and in addition shows a photodetector 18 mounted across terminals 8 and 9. A suitable photodetector could be a silicon photodiode which converts incident light into an electric current. It consists of a P-N junction in which the P junction is the anode and the N junction is the cathode. The underside of the silicon photodiode is the cathode and is completely metallized for securing to terminal 9. The anode terminal is on top and is secured to terminal 8. The conductive underside of photodetector 18 (cathode not shown) is secured to terminal 9 using for example conductive epoxy. The top conductive terminal 19 (anode) of photodetector 18 is secured to terminal 8 using a conductive clip 20 having one leg 21 of clip 20 extended and secured to terminal 8 while the other leg 22 is extended in the other direction and is secured to conductive terminal 19. Using this Z type shaped conductive clip 20 provides a physical securing means to further secure photodetector 18 onto the printed circuit sheet. Specifically, leg 22 of clip 20 can physically contact and exert pressure against photodetector 18 thereby further physically securing photodetector 18 onto the printed circuit sheet. Other types of securing means may be used to electrically connect the anode 19 to terminal 8.

Figure 3:
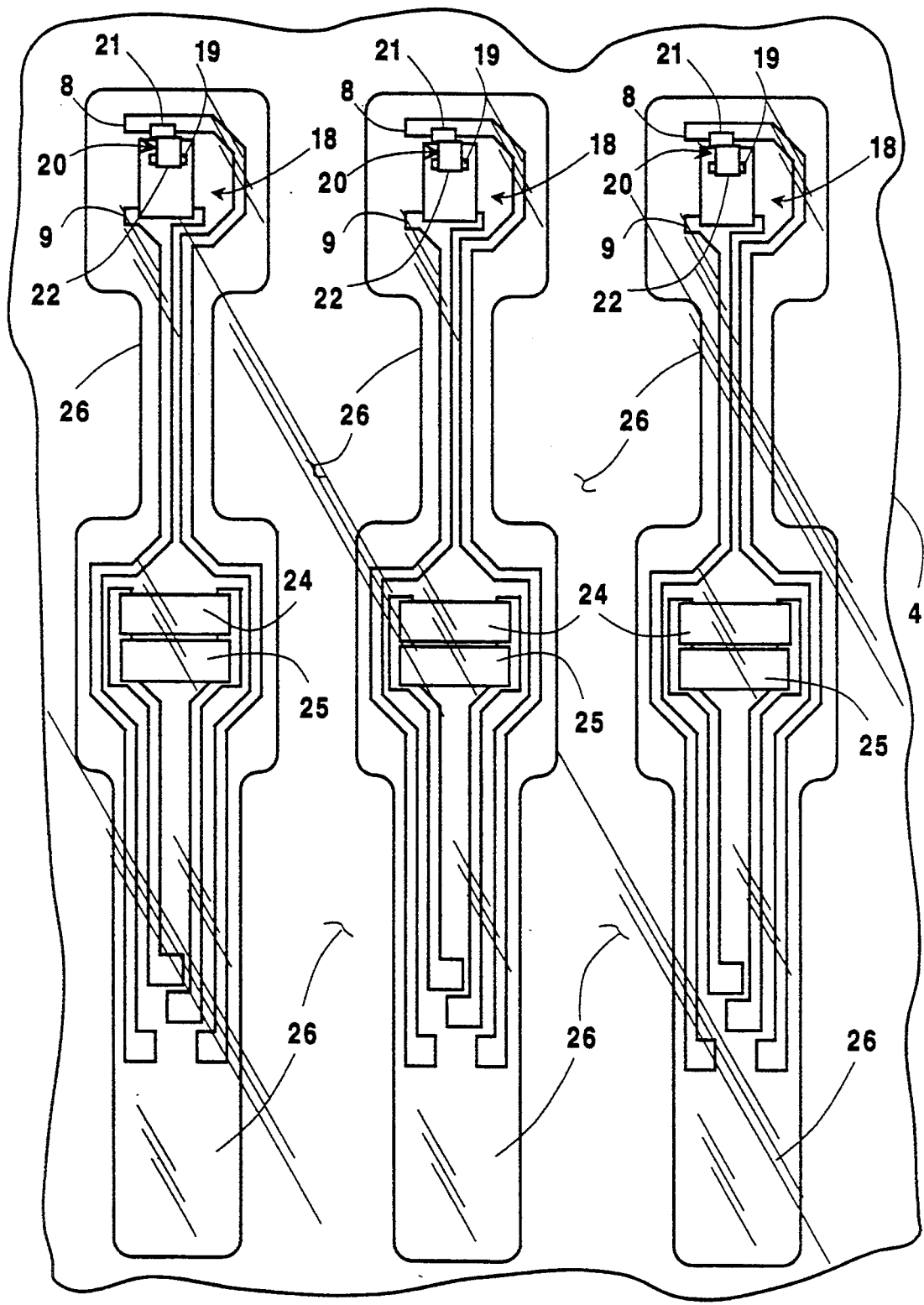
FIG. 3 is a plan view of the printed circuit sheet of FIG. 2 having a non-conductive layer secured over the circuits and components.

A pair of light emitting diodes 24-25 are connected in parallel across terminals 14 and 15. Again conductive epoxy could be used as the preferred securing means for electrically and physically securing the diodes 24-25 to the printed circuit sheet. As shown in FIG. 2, terminals 10 and 11 are adapted for electrically connecting the photodetector 18 to an oximeter not shown. In a similar manner, terminals 16 and 17 are adapted for electrically connecting the light emitting diodes 24 and 25 to an oximeter not shown. FIG. 3 shows the component-mounted printed circuit sheet of FIG. 2 with a non-conductive sheet or tape 26 secured over the components and circuitry to provide for electrical isolation and to effectively eliminate the moisture problem that could result from handling the printed circuit sheet.

Figure 4:
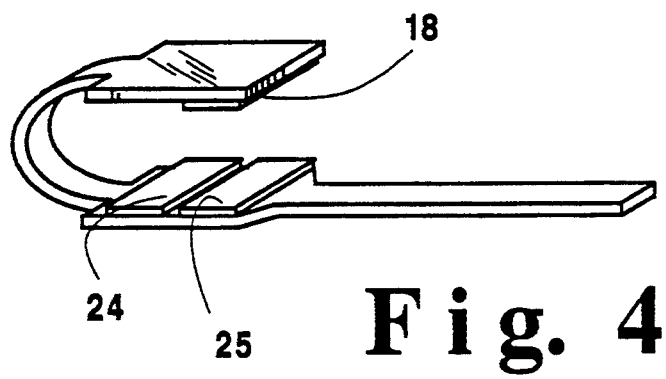
FIG. 4 is a perspective view of only one component-mounted circuit from the printed circuit sheet of FIG. 3 shown folded so that the photodetector is aligned over the diodes.

After the non-conductive tape 26 is secured over the printed circuit sheet, individual circuits 2 are punched or cut from the sheet. FIG. 4 shows an individual circuit sensor 2, without showing the printed circuit, that had been cut from the sheet and folded so that photodetector 18 is spaced apart from and facing diodes 24-25. In this manner, the individual circuit sensor 2 could be connected to an appropriate oximeter via terminals 10-11 and 16-17 and placed over a patient's tissue such as a finger or ear to measure certain characteristics of the blood in the tissue.

Figure 5A:
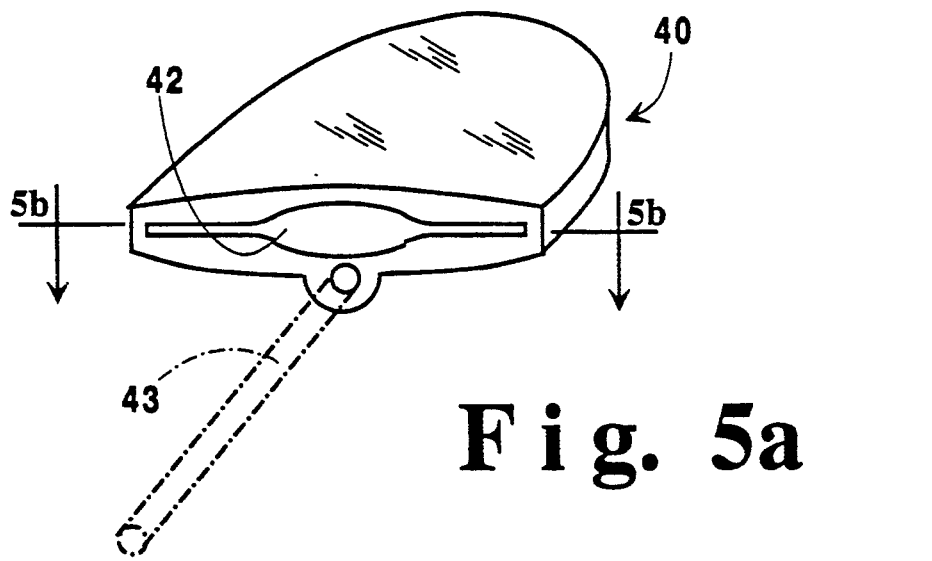
FIG. 5a is a perspective view of a finger pouch designed to accommodate the component-mounted circuit of FIG. 4.
Figure 5B:
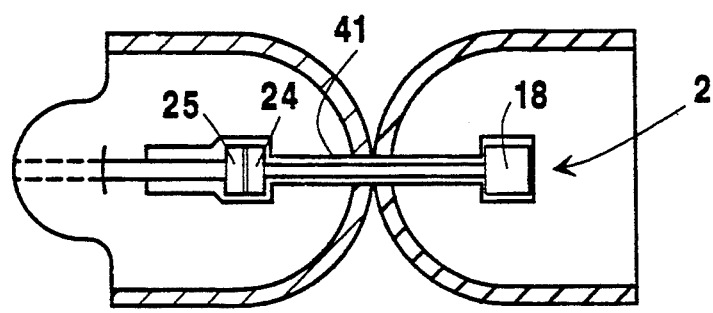
FIG. 5b is a cut open view of the finger pouch of FIG. 5a taken along line 5b-5b and containing the component mounted-circuit of FIG. 4.

When intended for use with a finger, the individual circuit sensor 2 could be placed in a flexible finger pouch 40 as shown in FIG. 5a and FIG. 5b. Specifically, finger pouch 40 could be made of flexible silicon or the like and molded with a channel 41 suitable for seating circuit sensor 2. FIG. 5b shows finger pouch 40 cut open to expose channel 41 but in the normal embodiment, the finger pouch 40 in FIG. 5b would be folded upon itself as shown in FIG. 5a so that finger pocket 40 would be provided in which the circuit sensor 2 would be flush mounted in the channel 41. As shown in FIG. 5a, pocket 40 has an opening 42 to accommodate a finger. The external connections from an oximeter is shown in broken lines 43 and the wires of the oximeter could be connected to terminals 10-11 and 16-17 of sensor 2 as discussed above.

EXAMPLE

A five inch wide roll of Mylar (polyester) was used as the sheet for the flexible printed circuit sensor. The Mylar sheet was then laminated with copper 0.0014 inch thick and then a photoresist was placed over the copper. The photoresist used was DuPont-4215, obtained from DuPont. The photoresist coated copper sheet was heated to about 240° F. at 2 feet per minute under 40 psi air pressure to adhere the photoresist to the copper. A negative containing an image of the circuits shown generally in FIG. 1 was then placed over the photoresist and an ultra-violet light was used to polymerize the photoresist with the circuit image. The pattern was developed using a sodium carbonate aqueous solution. The excess copper not covered by the circuitry image was etched with cupric chloride thereby removing the copper and leaving a plurality of copper circuits covered by the photoresist. The photoresist was then stripped off leaving a plurality of copper circuits as basically shown in FIG. 1. A conductive epoxy was dispensed onto the terminals of the individual circuits and then a robotic machine was used to place a silicon photodiode component across one pair of terminals and two light emitting diodes across another pair of terminals so that the diodes were connected in parallel as shown in FIG. 2. A Z type shaped electrical connector was used to connect the top polarity of the silicon photodiode (anode) to one set of terminals as generally shown in FIG. 2. The parallel connected light emitting diodes consisted of one red light emitting diode and one infra-red light emitting diode. The conductive epoxy used to secure the components to the circuitry was type H35-175 MPT which is a thermally curing epoxy from Epoxy Technology, Inc. Polytetrafluoroethylene tape was then applied over the circuitry and components mounted on the circuitry. The individual circuits were then punched out using a pneumatically driven punch and die.

Each of several of the individual circuits were placed within a finger pouch as basically shown in FIGS. 5a and 5b and then connected to electrical wires from an oximeter. Each finger pouch containing the printed circuit sensor connected to an oximeter was tested on several patients' fingers and found to present no problem in providing the oximeter with the information detected in the tissue of the patients. The non-conductive tape provided an insulation layer for the components and circuitry which prevented any moisture from the patients from shorting out the circuit. The securing of the components directly onto the copper layered sheet provided stability for the components and enabled the finger pouch to be used repeatedly without any problems. The Z type shaped connection pair also provided an additional restraining means for securing the silicon photodiode to the printed circuit sheet.

Although the foregoing invention is described in some detail by way of illustrations and example for purpose of clarity of understanding, it is understood that certain changes and modifications may be practiced and equivalents employed within the spirit of the invention as limited only by the scope of the appended claims.

What is claimed:

1. A flexible sensor assembly for detecting optical pulses comprising a flexible sheet containing conductive circuitry secured thereon, said conductive circuitry comprising a first pair of conductive strips insulated from each other and extending at one end to provide a first set of terminals and at the other end to provide a second set of terminals, and a second pair of conductive strips insulated from each other and from the first pair of conductive strips and extended at one end to provide a first set of terminals and at the other end to provide a second set of terminals with said second set of terminals spaced apart from the second set of terminals of the first pair of conductive strips; at least one photodetector mounted across and physically and electrically secured by a conductive clip to said first set of terminals of the first pair of conductive strips, at least one light emitting diode mounted across said first set of terminals of the second pair of conductive strips; an insulative tape secured over the photodetector, the light emitting diode and circuitry at least up to the second set of terminals of said first and second pair of conductive strips; and wherein said flexible sensor assembly is capable of being folded so that the photodetector can be spaced from and disposed over the light emitting diode.

2. The flexible sensor of claim 1 wherein only one photodetector is mounted across said first set of terminals of the first pair of conductive strips.

3. The flexible sensor of claim 1 wherein two light emitting diodes are mounted across said first set of terminals of the second pair of conductive strips and said light emitting diodes are mounted in parallel.

4. The flexible sensor of claim 3 wherein one light emitting diode is a red light emitting diode and the other diode is an infra-red light emitting diode.

5. The flexible sensor of claim 1 wherein said flexible sheet is selected from the group consisting of a polyester and a polyamide sheet.

6. The flexible sensor of claim 5 wherein said polyester sheet is from 0.0015 inch to 0.010 inch thick.

7. The flexible sensor of claim 1 wherein said insulative tape is polytetrafluoroethylene tape.

8. The flexible sensor of claim 7 wherein said polytetrafluoroethylene tape is from 0.0005 inch to 0.003 inch thick.

9. The flexible sensor of claim 1 wherein the conductive circuitry is copper.

10. The flexible sensor of claim 1 secured within a finger pouch having a first wall spaced apart from a second wall to define an opening to accommodate a finger, said photodetector secured to the first wall; said light emitting diode secured to the second wall and wherein said photodetector is spaced apart and aligned over the light emitting diode.

* * * * *